United States Patent [19]

Merger et al.

[11] 4,045,456

[45] Aug. 30, 1977

[54] MANUFACTURE OF ANTHRAQUINONES

[75] Inventors: Franz Merger, Frankenthal; Theodor Jacobsen, Limburgerhof; Heinz Eilingsfeld, Frankenthal; Ernest Miesen; Gerhard Nestler, both of Ludwigshafen, all of Germany

[73] Assignee: BASF Aktiengesellschaft, Ludwigshafen (Rhine), Germany

[21] Appl. No.: 693,515

[22] Filed: June 7, 1976

[30] Foreign Application Priority Data

June 20, 1975 Germany .............................. 2527491

[51] Int. Cl.² .............................................. C09B 1/00
[52] U.S. Cl. .................................................... 260/369
[58] Field of Search ........................................ 260/369

[56] References Cited

U.S. PATENT DOCUMENTS

| 2,401,225 | 5/1946 | Caesar et al. | 260/369 |
| 2,871,244 | 1/1959 | Kamlet | 260/369 |
| 2,967,187 | 1/1961 | Serres et al. | 260/369 |
| 3,032,560 | 5/1962 | Dawsey | 260/369 |
| 3,173,759 | 3/1965 | Williams | 260/369 X |
| 3,173,913 | 3/1965 | Van der Stelt | 260/369 X |

*Primary Examiner*—Paul F. Shaver
*Attorney, Agent, or Firm*—Keil, Thompson & Shurtleff

[57] ABSTRACT

Anthraquinones are manufactured by cyclizing o-benzoylbenzoic acids in the presence of oxygen-containing compounds of aluminum and silicon at elevated temperatures. The products are starting materials for the manufacture of dyes.

13 Claims, No Drawings

MANUFACTURE OF ANTHRAQUINONES

The present invention relates to a process for the manufacture of anthraquinones by cyclizing o-benzoylbenzoic acids in the presence of oxygen-containing compounds of aluminum and silicon, at elevated temperatures.

The conversion of benzoylbenzoic acid and substituted benzoylbenzoic acids to the corresponding anthraquinones in the presence of an excess of concentrated sulfuric acid (85 to 100 per cent strength) or weak oleum (5 to 20 per cent strength) at elevated temperatures has been disclosed (Ullmanns Encyklopaedie der Technischen Chemie (3rd edition), volume 3, pages 659 et seq. (1953); Kirk-Othmer, Encyclopedia of Chemical Technology, 2 (1963), pages 431 et seq.). Depending on the benzoylbenzoic acid to be cyclized and on the appropriately chosen strength of the cyclizing agent, the reaction is carried out at from 85° to 150° C, with reaction times of from one to two hours after addition of the acid to be cyclized.

An essential disadvantage of this intrinsically simple and cheap method of cyclization is the large amount of sulfuric acid or oleum, which — particularly during working up, where the mixture must be diluted with water — requires a large amount of space, causes corrosion, and must either be reprocessed or destroyed. The disposal of the waste waters from the process prevents a further problem.

Attempts have been made to overcome these defects of the process by using only small amounts of condensing agent (German Pat. No. 1,004,599; U.S. Pat. No. 2,842,562; British Pat. No. 765,036). However, for this purpose it is necessary to heat the reaction mixture to very high temperatures. The combination of the water eliminated and the acid added, however, is extremely corrosive under these conditions and furthermore the reaction mixture begins to decompose.

The use of phosphoric acid, aromatic sulfonic acids, eg. toluenesulfonic acid, chlorosulfonic acid, hydrofluoric acid or metal chlorides and metal bromides as cyclizing agents has also been disclosed (German Pat. No. 1,004,599). In these cases it is again necessary to heat the reaction mixture to high temperatures. The combination of the water eliminated and the cyclizing agents employed, however, is extremely corrosive under these conditions, and decomposition products are formed. All these processes are unsatisfactory from the point of view of simple, economical and safe operation and protection of the environment.

We have found that anthraquinones of the formula

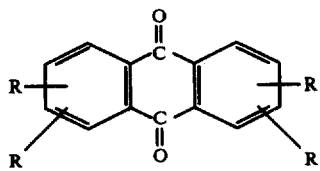

I where the individual R's are identical or different and each is hydrogen, halogen or alkyl, are obtained in an advantageous manner by cyclizing an o-benzoylbenzoic acid of the formula

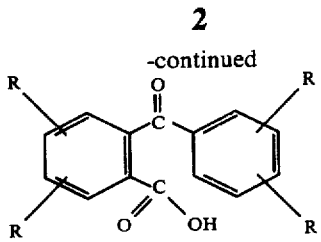

II where R has the above meanings, at elevated temperature, if the cyclization is carried out in the presence of an oxygen-containing compound of aluminum and of silicon at from 150° to 400° C.

Where o-benzoylbenzoic acid is used, the reaction can be represented by the following equation:

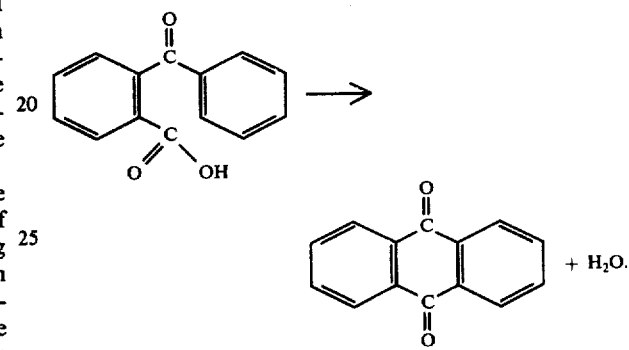

Compared to the conventional processes, the process of the invention gives anthraquinones more simply and more economically, and in good yield and with improved purity. Sulfonation of the anthraquinone nucleus of course does not occur. The involved working-up with substantial amounts of acid and/or water is avoided. In contrast to $H_2SO_4$, the cyclizing agent is not consumed (or deactivated) under the conditions of the invention by the water which is produced, and can be employed in smaller amounts and be fully reactivated in a simple manner, after prolonged periods of operation, by treatment with oxygen (air). The end product can easily be isolated in the pure form, eg. in the particularly preferred embodiment, by sublimation during the reaction. Significant corrosion of the equipment does not occur. The process creates less pollution of the environment and, as regards the purification of the waste water, is simpler, more reliable and more economical. These advantageous results are surprising in view of the prior art.

Preferred starting materials II and, accordingly, preferred end products I are those in which the individual R's may be identical or different and each is hydrogen, chlorine or bromine or straightchain or branched alkyl of 1 to 4 carbon atoms. Examples of suitable starting materials II are 3-chloro-, 4-chloro-, 5-chloro-, 6-chloro, 4,6-dichloro-, 5,6-dichloro-, 4,4'-dichloro-, 6,2'-dichloro-, 6,4'-dichloro-, 6,2',5,5'-tetrachloro-, 4-bromo, 6-chloro-3-methyl-, 4'-chloro-4-methyl, 4-methyl-, 4-ethyl- and 3,4-dimethyl-o-benzoylbenzoic acid, and o-(4-methyl-benzoyl)-, o-(4-ethyl-benzoyl)-, o-(2-chloro-benzoyl)- and o-(3-chloro-benzoyl)-benzoic acid, but especially o-benzoylbenzoic acid and o-(4-chloro-benzoyl)-benzoic acid.

The cyclization is carried out at from 150° to 400° C, under atmospheric or superatmospheric pressure or, advantageously, under reduced pressure, batchwise or, preferably, continuously. The preferred temperatures are from 200° to 350° C if the process is carried out in the melt and from 150° to 250° C if organic solvents are used. If the reaction is carried out continuously over a fixed bed of the cyclizing agent, a temperature of from 200° to 350° C, preferably from 250° to 300° C, and a pressure of from 1 to 200 mm Hg, preferably from 5 to 100 mm Hg, is preferred. For continuous cyclizations in a fluidized bed reactor, the preferred temperature range is from 250° to 350° C, especially from 280° to 330° C, and the pressure is advantageously from 10 to 50 mbars. When using the organic solvents, which can be used advantageously to form a suspension of the catalyst, such solvents may be any which are inert under the reaction conditions, preferably aliphatic hydrocarbons, eg. petroleum ether, naphtha, n-heptane, 2-ethylhexane, n-octane and nonane, and especially high-boiling chlorinated aliphatic or aromatic hydrocarbons, eg. 1,1,2,2-tetrachloroethane, 1,1,2,2-tetrachloroethylene, monochlorobenzene, dichlorobenzene and trichlorobenzene. In general, the amount of organic solvent used is from 85 to 400 per cent by weight, based on starting material II. The solvents can be re-used, if necessary after a preliminary treatment.

The oxygen-containing compounds of aluminum and silicon are suitably aluminum/silicon oxides, but preferably aluminum silicates and advantageously those which contain aluminum and silicon, in the oxide form, in amounts of from 0.01 to 10, preferably from 0.05 to 5, moles of aluminum oxide ($Al_2O_3$) per mole of silicon dioxide. For the purpose of calculating these ratios, the oxidic aluminum/silicon compounds or aluminum silicates are assumed to contain the oxides $Al_2O_3$ and $SiO_2$, regardless of the actual structure and composition of the oxygen-containing compound used. The said cyclizing agents may in addition contain alkali metal compounds or alkaline earth metal compounds, eg. the corresponding oxides or silicates. Examples of the above catalysts are aluminum silicate, magnesium aluminum silicate, dimagnesium aluminum silicate, sodium aluminum silicate, calcium aluminum silicate and — especially when the two elements are present in the above ratio of their oxides — fuller's earth, clays, kaolin, allophanes, zeolites, mullite, bentonite, kaolinite, montmorillonite, nontronite, beidellite, hectorite, glauconite and attapulgite, and appropriate activated or regenerated bleaching earths containing the above ratios of $Al_2O_3$ and $SiO_2$, eg. the bleaching earths described in Ullmanns Encyklopadie der Technischen Chemie, volume 4, pages 542 - 545. It is also possible to use synthetic aluminum silicates, eg. obtained by precipitation of aluminates with hydrated silicic acid or alkali metal silicate solutions or by precipitation of mixtures of aluminum salts and waterglass or silicic acid sol with ammonia or by fusing aluminosilicates, eg. kaolin or feldspars or alumina minerals, eg. bauxite, with silicic acid and alkali metal hydroxides or alkali metal carbonates, and subsequently leaching the melt with water. When the catalysts are used in the presence of solvents, eg. when catalyst suspensions are used, a particle size of from 0.01 to 2 millimeters, in particular from 0.05 0.1 millimeter, and a specific total surface area of the cyclizing agent of from 50 to 500 square meters per gram, are preferred. The term specific total surface area is used to describe the total internal and external surface area of the cyclizing agent, per gram of the latter. The specific total surface area can be determined by the conventional methods for determining the total surface area of catalysts, eg. the BET method (Ullmanns Encyklopaedia der Technischen Chemie, volume 9, page 266). The internal surface area of the cyclizing agent is advantageously from 50 to 500, especially from 150 to 400, $m^2/g$. If a fluidized bed process is used, particle sizes of from 0.05 to 1, preferably from 0.1 to 0.5. millimeters and a specific total surface area of from 50 to 500 $m^2/g$, are advantageous. In general, the radius of the pores of the cyclizing agent should be from 15 to 100 A, and advantageously from 30 to 80 A. If a fixed bed process is used, the particle sizes are advantageously from 0.5 to 10, preferably from 1.5 to 3, millimeters. The shape of the particles is optional; eg., powders, extrudates, spheres or granules may be used.

In suspension, the reaction may be carried out as follows: a mixture of the starting material II, cyclizing agent and a solvent is kept at the reaction temperature for from 0.5 to 10 hours and preferably from 1 to 5 hours. The end product which separates out is then isolated from the reaction mixture by conventional methods. For example it is possible to cool the mixture, eg. to from 100° to 120° C, filter off the end product together with the catalyst and finally isolate the end product with the aid of a solvent, eg. ethanol. The solvents may be re-used, if necessary after a preliminary treatment.

In general, however, a continuous process will be preferred. For this it is advantageous to use the cyclizing agent as a fixed bed, without using a solvent, and to introduce the starting material II, which has been heated to above its melting point, by spraying it into the catalyst zone, which is kept at the reaction temperature. Residence times of from 0.01 to 60 seconds, and in particular from 0.1 to 10 seconds, are advantageous. The end product formed sublimes off continuously and may be isolated in a pure crystalline form by cooling, and, if appropriate, also adding water.

In a further preferred embodiment, the cyclizing agent is employed, in the form of chips, grit or spheres, in a fluidized bed, the size of the catalyst particles being advantageously from 0.5 to 1.0 mm and especially from 0.1 to 0.5 mm. The height of the catalyst bed is advantageously so chosen that the resulting residence times of the starting materials II in the catalyst bed are from 0.01 to 20 seconds and preferably from 0.1 to 10 seconds. Advantageously, gases which are inert under the reaction conditions, eg. argon, nitrogen or ethane, or gas mixtures, eg. air, may also be admixed to the fused starting material II, or the fluid starting material II may be sprayed into such gases, in order to achieve fluidization of the bed. In general, from 0.1 to 10, preferably from 1 to 5, moles of inert gas may be used per mole of starting material II. The fluidizing gas used is advantageously air or, preferably, an inert gas, eg. nitrogen, carbon dioxide or argon, in general in amounts of from about 100 to 1,000 l/hour, preferably from 300 to 600 l/hour. The process of the invention may be carried out in a simple or a subdivided fluidized bed system, which may be open or closed and may or may not utilize circulation of the fluidized dust. Details of the reactors, method of operation, process variants and reaction conditions used for fluidized bed processes are to be found in Ullmanns Encyklopaedia der Technischen Chemie, volume 1, pages 916 et seq. The reaction mixture is worked up in the manner described earlier.

The compounds which may be manufactured by the process of the invention are valuable starting materials for the manufacture of dyes. Regarding their use, reference may be made to the cited publications.

In the Examples, parts are by weight and bear the same relation to parts by volume as that of the gram to the liter.

EXAMPLE 1

A vertical tube which is surrounded with a heating jacket is filled with 80 parts of aluminum silicate extrudate (45% by weight of $Al_2O_3$ and 55% by weight of $SiO_2$; $\phi$ 1.5 mm) and is heated to 300° C and pumped out to a pressure of 5 mm Hg. The specific total surface area of the cyclizing agent is 200 square meters per gram. Per hour, 32.5 parts of fused o-benzoylbenzoic acid are charged onto the catalyst. The anthraquinone formed, which sublimes off immediately, is condensed in a cooled vessel at the bottom end of the tube. The conversion is practically quantitative. Per hour, 28.4 parts (95% of theory) of anthraquinone of melting point 283° - 285° C are obtained.

EXAMPLE 2

A fluidized bed reactor equipped with a heating jacket is filled with 70 parts of aluminum silicate grit (25% by weight of $SiO_2$ and 75% by weight of $Al_2O_3$; $\phi$ from 0.1 to 0.3 mm) and is heated to 305° C. The specific total surface area of the cyclizing agent is 400 square meters per gram. The catalyst is kept fluidized by means of 300 parts by volume of nitrogen/hour. Per hour, 70 parts of o-(4-chlorobenzoyl)-benzoic acid are fed into the reactor. The β-chloroanthraquinone formed is precipitated by scrubbing the stream of gas with water. The conversion is practically quantitative. Per hour, 62 parts (95% of theory) of β-chloroanthraquinone of melting point 203° to 205° C are obtained.

We claim:

1. A process for the manufacture of anthraquinones of the formula

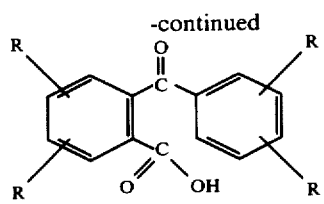

I where the individual R's may be identical or different and each R is selected from the group consisting of hydrogen, halogen and alkyl, by cyclizing an o-benzoylbenzoic acid of the formula

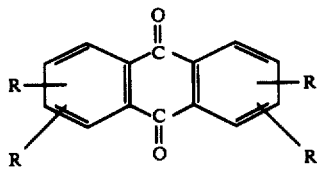

II

-continued where R has the above meanings, at elevated temperatures, in which the cyclization is carried out in the presence of a cyclizing agent of an oxygen-containing compound of aluminum and of silicon at a temperature of from 150° to 350° C.

2. A process as claimed in claim 1, wherein the reaction is carried out in the melt at from 200° to 350° C.

3. A process as claimed in claim 1, wherein the reaction is carried out in the presence of organic solvents at from 150° to 250° C.

4. A process as claimed in claim 1, wherein the reaction is carried out continuously over the cyclizing agent in a fixed bed at from 200° to 350° C.

5. A process as claimed in claim 1, wherein the reaction is carried out continuously in a fluidized bed reactor at from 250° to 350° C.

6. A process as claimed in claim 1, wherein the reaction is carried out in the presence of organic solvents by means of which the catalyst can be suspended.

7. A process as claimed in claim 1, wherein the reaction is carried out with aluminum silicates.

8. A process as claimed in claim 1, wherein the reaction is carried out with aluminum and silicon in the form of oxides, using from 0.01 to 10 moles of aluminum oxide ($Al_2O_3$) per mole of silicon dioxide.

9. A process as claimed in claim 1, wherein the reaction is carried out in the presence of solvents, using catalyst suspensions wherein the particle size is from 0.01 to 2 mm and the specific total surface area of the cyclizing agent being from 50 to 500 square meters per gram.

10. A process as claimed in claim 1, wherein the reaction is carried out by the fluidized bed process, the particle sizes of the cyclizing agent being from 0.05 to 1 mm and the specific total surface area of the cyclizing agent being from 50 to 500 m²/g.

11. A process as claimed in claim 1, wherein the reaction is carried out with a cyclizing agent in which the radius of the pores is from 15 to 100 A.

12. A process as claimed in claim 1, wherein the reaction is carried out by a fixed bed process, the particle sizes of the cyclizing agent being from 0.5 to 10 mm.

13. A process according to claim 1, wherein the residence times of the starting materials II in the catalyst bed, when carrying out the reaction, are from 0.01 to 20 seconds.

* * * * *